United States Patent
Orbach

(10) Patent No.: US 12,205,685 B2
(45) Date of Patent: *Jan. 21, 2025

(54) COMPUTERIZED INTERACTIVE PSYCHOLOGICAL ASSESSMENT PROTOCOL—iPAP

(71) Applicant: Tuvi Orbach, London (GB)

(72) Inventor: Tuvi Orbach, London (GB)

(*) Notice: Subject to any disclaimer, the term of this patent is extended or adjusted under 35 U.S.C. 154(b) by 0 days.

This patent is subject to a terminal disclaimer.

(21) Appl. No.: 18/494,967

(22) Filed: Oct. 26, 2023

(65) Prior Publication Data

US 2024/0055083 A1 Feb. 15, 2024

Related U.S. Application Data

(63) Continuation of application No. 17/966,474, filed on Oct. 14, 2022, now Pat. No. 11,837,338, which is a
(Continued)

(51) Int. Cl.
*G09B 7/00* (2006.01)
*G16H 10/20* (2018.01)

(52) U.S. Cl.
CPC ............... *G16H 10/20* (2018.01); *G09B 7/00* (2013.01)

(58) Field of Classification Search
CPC .................................. G09B 7/00; G16H 10/20
See application file for complete search history.

(56) References Cited

U.S. PATENT DOCUMENTS

| 4,699,153 A | 10/1987 | Shevrin et al. |
| 6,030,226 A * | 2/2000 | Hersh ...................... A61B 5/16 434/156 |

(Continued)

FOREIGN PATENT DOCUMENTS

CN 201310203098 8/2013

OTHER PUBLICATIONS

Jeff Conklin, Ph.D., "Dialogue Mapping: Building Shared Understanding of Wicked Problems," Chapter 1, Wiley, Oct. 2005.
(Continued)

*Primary Examiner* — Omkar A Deodhar
*Assistant Examiner* — Shauna-Kay Hall
(74) *Attorney, Agent, or Firm* — Barich IP Law Group

(57) ABSTRACT

To efficiently assess, prioritize, and re-assess individuals respectively for intervention OR for ongoing programs/activities OR for personalized rehabilitation or training activities: A Computerized Interactive Psychological Assessment Protocol including the steps of: using a predetermined interactive media, interfacing with a client, (A) accepting some predetermined goal-relevant self-assessment responses from the client, regarding the client's respective motivation, belief, know-how, state-of-mind, activity, etc.; (B) accepting self-characterization responses from the client, regarding the client's respective personality; (C) preferably electronically characterizing the responses according to at least one metric from the list: client's response time, client's preference, among interactive task/query modes, and client's respective response physiology; and (D) electronically storing a data representation of the responses and characterizations, along with a time stamping, for use in a longitudinal analysis of the client psychological development.

20 Claims, 3 Drawing Sheets

Related U.S. Application Data continuation of application No. 17/067,239, filed on Oct. 9, 2020, now Pat. No. 11,501,855, which is a continuation of application No. 15/203,736, filed on Jul. 6, 2016, now Pat. No. 10,839,944.

(60) Provisional application No. 62/289,872, filed on Feb. 1, 2016.

(56) References Cited

U.S. PATENT DOCUMENTS

| | | | |
|---|---|---|---|
| 7,207,804 B2 * | 4/2007 | Hersh | G09B 5/065 |
| | | | 434/323 |
| 2004/0116778 A1 | 6/2004 | Mauldin | |
| 2004/0210159 A1 * | 10/2004 | Kibar | A61B 5/165 |
| | | | 128/898 |
| 2005/0117527 A1 | 6/2005 | Williams et al. | |
| 2007/0254270 A1 | 11/2007 | Hersh | |
| 2010/0009325 A1 * | 1/2010 | Afanasiev | G09B 19/00 |
| | | | 434/236 |
| 2010/0055658 A1 * | 3/2010 | Sturm | G09B 7/00 |
| | | | 434/350 |
| 2011/0020778 A1 | 1/2011 | Forbes | |
| 2011/0118555 A1 * | 5/2011 | Dhumne | A61M 21/02 |
| | | | 600/300 |
| 2012/0035428 A1 | 2/2012 | Roberts | |
| 2012/0071785 A1 * | 3/2012 | Forbes | G06Q 30/02 |
| | | | 600/558 |
| 2013/0035946 A1 | 2/2013 | Ratan et al. | |
| 2013/0066968 A1 | 3/2013 | Ziegler | |
| 2013/0073474 A1 | 3/2013 | Young | |
| 2014/0106318 A1 * | 4/2014 | Wright | G09B 7/02 |
| | | | 434/219 |
| 2014/0214709 A1 * | 7/2014 | Greaney | G06Q 10/1053 |
| | | | 705/321 |
| 2015/0262499 A1 | 9/2015 | Wicka et al. | |
| 2016/0132604 A1 * | 5/2016 | Brust | G16H 50/20 |
| | | | 707/722 |
| 2016/0283678 A1 | 9/2016 | Ram | |

OTHER PUBLICATIONS

Ricardo Matsumura de Araujo, "Memetic Networks: problem-solving with social network models", Dec. 2010.

Muhammad Z.C. Candra, Hong-Linh Truong, and Schahram Dustdar, "Provisioning Quality-aware Social Compute Units in the Cloud," Distributed Systems Group, Vienna University of Technology, 2013.

Diane H. Sonnenwald, "Evolving Perspectives of Human Information Behavior: Contexts, Situations, Social Networks and Information Horizons," published in Exploring the Contexts of Information Behaviour, 1999.

* cited by examiner

| Internal name | W=will | C=Confidence | A=Action | User category |
|---|---|---|---|---|
| 1. Not willing, not ready | Neg <13 | Neg <13 | N <13 | Definitely not ready |
| 2. start will, no confidence, no action | Pos 13-17 | Neg <13 | N <13 | Not ready+ |
| 3. will, no confidence, no action | Very P 18-20 | N <13 | N <13 | Will but not ready + |
| 4. no will, start confidence, no action | N <13 | Pos 13-17 | N <13 | Confident, but not ready |
| 5. Confidence, no action | Pos 13-17 | Pos 13-17 | N <13 | Getting ready |
| 6. will, confidence, no action | Very P 18-20 | Pos 13-17 | N <13 | Getting ready+ |
| 7. no will, high confidence, no action | N <13 | Very P 18-20 | N <13 | Thinking of getting ready |
| 8. Start will, high confidence, no A | Pos 13-17 | Very P 18-20 | N <13 | Getting ready |
| 9. High W, high C, no A | Very P 18-20 | Very P 18-20 | N <13 | Ready + |
| 10. No W, no C, start A | Neg <13 | Neg <13 | Pos 13-17 | Unauthentic Action |
| 11. Start W, no C, start A | Pos 13-17 | Neg <13 | Pos 13-17 | Active, no confidence |
| 12. High W, no C, start A | Very P 18-20 | Neg <13 | Pos 13-17 | Willing and Active, no C |
| 13. No W, start C, start A | N <13 | Pos 13-17 | Pos 13-17 | Unauthenticated Action |
| 14. Start W, start C, start A | Pos 13-17 | Pos 13-17 | Pos 13-17 | Ready and start Action |
| 15. High W, start C, start A | Very P 18-20 | Pos 13-17 | Pos 13-17 | Ready |
| 16. No W, high C, start A | Neg <13 | Very P 18-20 | Pos 13-17 | Unauthenticated start A, with C |
| 17. Starting W, High C, start A | Pos 13–17 | Very P 18-20 | Pos 13-17 | Ready ++ |
| 18. High W, high C, start A | Very P 18-20 | Very P 18-20 | Pos 13-17 | Active |
| 19. No W, no C, high A | Neg <13 | Neg <13 | Very P 18-20 | Unauthenticated, no C |
| 20. Start W, no C, high A | Pos 13-17 | Neg <13 | Very P 18-20 | Active, no C |
| 21. High W, no C, high A | Very P 18-20 | Neg <13 | Very P 18-20 | Active and willing, no C |
| 22. No W, start C, high A | Neg <13 | Pos 13-17 | Very P 18-20 | Unauthenticated Action, with C |
| 23. Start W, start C, high A | Pos 13-17 | Pos 13-17 | Very P 18-20 | Active + |
| 24. High W, start C, high A | Very P 18-20 | Pos 13-17 | Very P 18-20 | Active ++ |
| 25. No W, high C, high A | Neg <13 | Very P 18-20 | Very P 18-20 | Unauthenticated A, with C |
| 26. Start W, high C, high A | Pos 13-17 | Very P 18-20 | Very P 18-20 | Action +++ |
| 27. The Best – High W, C and A | Very P 18-20 | Very P 18-20 | Very P 18-20 | Best ***** |

FIG. 4 - Table with 3 dimensions and user category for each entry

| Internal name | W | Will | C Level | Confidence | A Level | Action | Category |
|---|---|---|---|---|---|---|---|
| 1. Not willing, not ready | 0 | Neg <13 | 0 | Neg <13 | 0 | N <13 | Definitely not ready |
| 2. start will, no confidence, no | 1 | Pos 1317 | 0 | Neg <13 | 0 | N <13 | Not ready+ |
| 3. will, no confidence, no action | 2 | Very P 1820 | 0 | N <13 | 0 | N <13 | Will but not ready + |
| 4. no will, start confidence, no | 0 | N <13 | 1 | Pos 1317 | 0 | N <13 | Confident, but not |
| 5. Confidence, no action | 1 | Pos 1317 | 1 | Pos 1317 | 0 | N <13 | Getting ready |
| 6. will, confidence, no action | 2 | Very P 1820 | 1 | Pos 1317 | 0 | N <13 | Getting ready+ |
| 7. no will, high confidence, no | 0 | N <13 | 2 | Very P 1820 | 0 | N <13 | Thinking of getting |
| 8. Start will, high confidence, no A | 1 | Pos 1317 | 2 | Very P 1820 | 0 | N <13 | Getting ready |
| 9. High W, high C, no A | 2 | Very P 1820 | 2 | Very P 1820 | 0 | N <13 | Ready + |
| 10. No W, no C, start A | 0 | Neg <13 | 0 | Neg <13 | 1 | Pos 1317 | Unauthentic Action |
| 11. Start W, no C, start A | 1 | Pos 1317 | 0 | Neg <13 | 1 | Pos 1317 | Active, no |
| 12. High W, no C, start A | 2 | Very P 1820 | 0 | Neg <13 | 1 | Pos 1317 | Willing and Active, |
| 13. No W, start C, start A | 0 | Neg <13 | 1 | Pos 1317 | 1 | Pos 1317 | Unauthenticated |
| 14. Start W, start C, start A | 1 | Pos 1317 | 1 | Pos 1317 | 1 | Pos 1317 | Ready and start |
| 15. High W, start C, start A | 2 | Very P 1820 | 1 | Pos 1317 | 1 | Pos 1317 | Ready |
| 16. No W, high C, start A | 0 | Neg <13 | 2 | Very P 1820 | 1 | Pos 1317 | Unauthenticated |
| 17. Starting W, High C, start A | 1 | Pos 1317 | 2 | Very P 1820 | 1 | Pos 1317 | Ready ++ |
| 18. High W, high C, start A | 2 | Very P 1820 | 2 | Very P 1820 | 1 | Pos 1317 | Active |
| 19. No W, no C, high A | 0 | Neg <13 | 0 | Neg <13 | 2 | Very P 1820 | Unauthenticated, no |
| 20. Start W, no C, high A | 1 | Pos 1317 | 0 | Neg <13 | 2 | Very P 1820 | Active, no C |
| 21. High W, no C, high A | 2 | Very P 1820 | 0 | Neg <13 | 2 | Very P 1820 | Active and willing, no |
| 22. No W, start C, high A | 0 | Neg <13 | 1 | Pos 1317 | 2 | Very P 1820 | Unauthenticated |
| 23. Start W, start C, high A | 1 | Pos 1317 | 1 | Pos 1317 | 2 | Very P 1820 | Active + |
| 24. High W, start C, high A | 2 | Very P 1820 | 1 | Pos 1317 | 2 | Very P 1820 | Active ++ |
| 25. No W, high C, high A | 0 | Neg <13 | 2 | Very P 1820 | 2 | Very P 1820 | Unauthenticated A, |
| 26. Start W, high C, high A | 1 | Pos 1317 | 2 | Very P 1820 | 2 | Very P 1820 | Action +++ |
| 27. The Best – High W, C and A | 2 | Very P 1820 | 2 | Very P 1820 | 2 | Very P 1820 | Best ***** |

FIG. 5 - Table with 3 dimensions and user category and level enabling algorithmic calculation of row number

COMPUTERIZED INTERACTIVE PSYCHOLOGICAL ASSESSMENT PROTOCOL—iPAP

CROSS-REFERENCE TO RELATED APPLICATIONS

This application is a continuation of U.S. patent application Ser. No. 17/966,474, filed Oct. 14, 2022, entitled "Computerized Interactive Psychological Assessment Protocol—iPAP", which is a continuation of U.S. patent application Ser. No. 17/067,239, filed Oct. 9, 2020, entitled "Computerized Interactive Psychological Assessment Protocol—iPAP" now U.S. Issued U.S. Pat. No. 11,501,855, which is a continuation of U.S. patent application Ser. No. 15/203,736, filed Jul. 6, 2016, entitled "Computerized Interactive Psychological Assessment Protocol—iPAP", now U.S. Pat. No. 10,839,944, which claims priority to the U.S. Provisional Patent Application No. 62/289,872, filed Feb. 1, 2016, entitled "Computerized Interactive Psychological Assessment Protocol iPAP", all of which are hereby incorporated by reference in their entirety.

FIELD OF THE INVENTION

Generally, the present invention relates to computerized interactive psychological assessment of a client via a computer-controlled user interface. More specifically, the present invention relates to a protocol for assessment and reassessment of a client, and to intervention decisions occurring during the protocol.

BACKGROUND OF THE INVENTION

There are a few prior art patents that broadly define some applicable limits to the scope of the present invention, and these include: U.S. Pat. No. 7,207,804 application of multimedia technology to computer administered vocational personnel assessment: CN 201310203098 Entrepreneurship potential scene simulation evaluation system and evaluation method; and US 20110118555 System and method for screening, treating, and monitoring psychological conditions.

Within this scope, substantially because of the limited-time of professional psychological trainers, psychologists, psychiatrists, psychiatric nurses, psychotherapists, and the like, and substantially because of the ongoing increases in occurrences of stress, anxiety, depression, incorrect mindset, and other debilitating psychological conditions, there are needs in the art for an assessment protocol (1) that can be initiated for both initial assessment and for reassessment, and (2) that automatically categorizes and/or prioritizes the assessed individual clients for (A) immediate intervention, (B) ongoing programs and activities, and personalizes intervention, rehabilitation, and training activities. It should instantly be recognized that any improvement in the speed, efficacy, and/or associated costs of psychological profiling answers an ongoing need in the art.

Likewise, it should be appreciated that, in addition to "other debilitating psychological conditions", there are other needs in the art for an assessment protocol; such as to help individuals change habits and/or to achieve goals. For all of these instances (anxiety, depression, stress, changing habits, achieving goals, and the like), there is also an ongoing need for monitor progress of intervention, treatment, programs, and such. Thus, there is also an ongoing need for improvements in gathering, summarizing, and understanding changing personal information, which may be relevant to navigating and/or for providing interactive personalized intervention, and such.

Furthermore, there is a need in the art for a more robust computerized interactive psychological assessment protocol which incorporates co-factors, such as personality and/or physiology; and most importantly, that is amenable to longitudinal client-status review.

Notwithstanding, there remains a need for improvements for observing short term and long term changes (such as regarding dimensions and attributes—as will be described with regard to the present invention), especially so that the pace and type or method of any intervention can be adjusted to the client's actual current state. The pith-and-marrow of answering these needs will allow for client reassessment, and for micro-shift redirection of ongoing intervention; all of which represents improvements for intervention dynamics.

Turning now to a few broad terms used herein: client refers to a person undergoing assessment; trainer refers to a professional, or a trusted mentor (or a respective assistant thereto) who may review the assessment and/or may interact with the client; protocol refers to a method of steps between a multiplicity of entities—such as the client, the trainer, a computer & associated electronic memory system, respectively invoked software modules, a communications systems between any pair of the aforesaid entities, and respective audio, visual, and sensory peripherals substantially interfacing with any of the aforesaid entities; and "computer" refers to any electronic device which can process information, store information and present information to the user, including mobile phones, smart watches, etc.

BRIEF DESCRIPTION OF DRAWINGS

In order to understand the invention and to see how it may be carried out in practice, embodiments including the preferred embodiment will now be described, by way of non-limiting example only, with reference to the accompanying drawings. Furthermore, a more complete understanding of the present invention and the advantages thereof may be acquired by referring to the following description in consideration of the accompanying drawings wherein:

FIGS. 4 and 5 respectively illustrate exemplary algorithm decision tables.

SUMMARY OF THE INVENTION

Substantially addressing various aspects of the aforesaid needs in the art, "iPAP" hereinafter refers to "embodiments" of a computerized "interactive Psychological Assessment Protocol" according to the present invention. It should be noted that an iPAP is preferably for use in conjunction with a computerized interactive psychological intervention protocol; which, in turn, respectively includes ongoing iPAP in conjunction with any of: (A) immediate intervention and/or (B) ongoing—preferably computer-controlled—programs and activities, and/or (C) personalized- or group-participation-intervention, rehabilitation, and training activities. It should be appreciated that iPAP, being a computerized assessment, is easily amenable for ongoing micro-reassessment use for each client; a functional attribute that has been impractical for classical pencil and paper assessments, which were typically too cumbersome for any client's patient cooperation. Ongoing iPAP micro-reassessment focuses on issues which seem to be changing or which may correlate with observed changes (or with some observed issue intractability).

Figure 1:
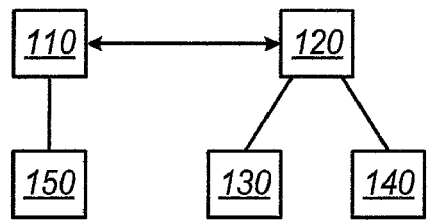
FIG. 1 illustrates a schematic view of a computerized interactive psychological assessment protocol.

Turning to FIG. 1, broadly defined, an iPAP includes the steps of: using (110) a predetermined interactive media interfacing (120) with a client (a) for at least one predetermined goal, accepting (130) goal-relevant self-assessment responses from the client, substantially regarding at least three [albeit preferably more] of the client's respective dimensions which are selected from the exemplary list (i) motivation, (ii) belief, (iii) know-how, (iv) capability, (v) state-of-mind, (vi) activity, and (vii) expectation (or probability) to achieve the at least one predetermined goal by a pre-specified time (or within a pre-specified period), [or (viii) the like—see note below]; (b) accepting (140) self-characterization responses from the client, substantially regarding the client's respective personality attributes and qualities; [preferably (c) electronically characterizing (130) a plurality of the responses according to at least one metric (albeit preferably a plurality, such as at least two or three) selected from the list (i) client's response time, (ii) client's preference for interactive task/query modes selected from the list written text, audio, images, icons, photographs, video, animation, mathematical equations, logic puzzles, games, music, songs, type of intervention, type of therapy, language, therapist/trainer gender/background/etc. (other characteristics of the trainer—be that a human trainer or a computerized trainer), time/duration of interactions, level of privacy of information (given or received), and other preferences suggested by the client/user, and (iii) client's respective response physiology, selected from at least one parameter characterizing client's voice, client's face topology, client's pupil dilation, client's eye tracking, client's GSR/EDA, client's skin-color, client's respiration, client's heart rate, client's heart rate variability, client's movements, client's brain waves, client's temperature, and a combination of any of the aforesaid (or the like);] and (d) electronically storing (150) a data representation of the responses and of the characterizations, along with a time stamping of at least one of the acceptings, for use in a longitudinal analysis of the client psychological development—thereby facilitating provision of assessments and of feedback with respect to the level and progress of the respective user's state in each of the aforementioned dimensions. Note: Regarding the above mentioned dimension "(viii)", the present invention is adaptive to other dimensional models, groupings, clustering, and organizations of self assessment, and mutatis mutandis regarding self characterization.

In that iPAP is goal oriented, it may be helpful for the reader to consider one of the following typical exemplary goals when considering various portions of the present invention. An exemplary goal may be: to overcome anxiety, to overcome depression, to improve aspects of wellbeing, to improve life quality, to change a habit (such as smoking or eating too many sweets), to find a partner, to get a job, to improve a relationship, to acquire a skill, to become successful in some area of endeavor, or the like. Accordingly, an iPAP goal for a specific user may be defined or chosen by the user, or with the help of an adviser or an organization. Similarly, iPAP may include assessments and protocols to help the user define a goal—with or without an adviser's guidance.

Comparing iPAP with reasonable combinations of prior art, most existing computerized assessments almost copy classical pencil and paper assessments and protocols; essentially just transforming those assessments to computer screen and input device (such as keyboard or touch-pad). IPAP represents a new generation of personalized computer assessment protocols, which customize and tailor to specific users and their respective situations. For example, iPAP individualizes the order (flow) of assessment questions according to user's respective answers and known needs; thereby circumventing sections of the classical pencil and paper assessment which may be respectively inappropriate.

Furthermore, various iPAP incorporate media that is not an emulation of paper, such as audio, photos, video, or animation—instead of or in addition to text.

More specifically, "using a predetermined interactive media interfacing with a client" relates to the respective audio, visual, and sensory peripherals substantially interfacing with any of the entities. These may include exemplary items, such as a computer or mobile phone screen, a computer mouse, a keyboard, a touch screen, a microphone, an audio speaker, audio headphones, virtual reality goggles, and the like; including examples described hereinafter. Of course, the interactive aspect is much stronger for some similar sensory pairings of exemplary peripherals than for others. Nevertheless, voice commands may result in tactile response, visual text may result in audio, response, essentially any stimulus may result in a physiological response, and the like. For example, pictures may be used to measure reaction times; such as those which represent a fear or phobia in the client or those which represent an attraction or arousal in the client.

More specifically, "(a) for at least one predetermined goal, accepting goal-relevant self-assessment responses from the client, substantially regarding at least three of the client's respective dimensions which are selected from the list (i) motivation, (ii) belief or confidence, (iii) know-how, (iv) capability, (v) state-of-mind, (vi) activity, and (vii) expectation to achieve the at least one predetermined goal by a pre-specified time;" relates to some milestone achievement ("goal") that has been externally negotiated between any pair of the entities (a client, a trainer/mentor/therapist/counselor, an iPAP enabled computer "module"), or agreed to by all of the entities, or (according to various constraints of the computer) selected by the client, or the like. Exemplary goals may be to achieve physical and/or behavioral changes (such as to stop smoking, drinking, drug use, fighting, or the like; to lose weight, to wake up for work, start and activity—such as search for a job, or the like) or they may be psychological (such as to feel less aggressive, more self confident, less depressed, happier, less stressed, motivated, or the like).

Self-assessment responses and relevant exemplary instances will be discussed at length in the Detailed Description of the Invention section (below). Please note that expectation relates to subjective belief and/or probability (or chance) to achieve the goal—as would be understood differently for a client wanting to lose a large amount of weight in a very short time compared to wanting to lose the same amount of weight over a comparatively very long time.

More specifically, "(b) accepting self-characterization responses from the client, substantially regarding the client's respective personality attributes and qualities;" relates firstly to the client's current self-image and secondly to changes to the client's self image, which may be caused by "spontaneous" positive-or-negative events in the client's life (such as change of employment, health, marital/relationship status, family, or the like); any of which may explain a change in the client's goal-relevant self-assessment, which might otherwise be interpreted as reflecting on the client's current psychological intervention success or failure. Exemplary instances of self-characterization will be discussed at length in the Detailed Description of the Invention section (below). Exemplary instances of intervention may be anything from referral to a Cognitive Behavioral Therapy group or individual program to recommendation to participation in formal or informal activities, such as dance, sport, meditation, job training, continuing education, volunteer work, or the like. Intervention is preferably dynamic, allowing for changes in speed, intensity, direction, and orientation according to changes observed in iterative micro reassessments—as will be further described below.

More specifically, "preferably (c) electronically characterizing a plurality of the responses according to at least one metric selected from the list (i) client's response time, (ii) client's preference for interactive task/query modes selected from the list written text, audio, images, icons, photographs, video, animation, mathematical equations, logic puzzles, games, etc. and (iii) client's respective response physiology, selected from at least one parameter characterizing client's voice, client's face topology, client's pupil dilation, client's eye tracking, client's GSR/EDA, client's changes of skin-color, client's respiration, client's heart rate, client's heart rate variability, client's movements, client's brain waves, client's temperature, and a combination of any of the aforesaid;" all relate to externally verifiable indicators reflecting the client's stress and emotions; often reflecting truthfulness of the answer, emotional sensitivity of the issue of inquiry or of the accomplishment of a task (per se), and the like. In the context of the present invention, "task/query" refers to a task (such as "use the touch-pad to move the object on the screen through the maze on the screen) and/or a query (such as "What is your name? (type here)") and/or a task/query (such as "select which of the answers A-B-C-or-D best reflects your mental alertness"), or the like. In the context of the present invention, sensors (camera, microphone, touch pad, and even physiology specific appurtenances) of smartphones, personal computers, and the like—may be employed to provide respective characteristic (e.g. emotion, heart rate variability, breathing rate, voice analysis, face expression analysis, etc.). Many aspects of respective physiological response provide cues and hints to a human interviewer—and iPAP is in fact enabled to collect (and thus enabled to analyze) these cues to a higher precision than most human "consultants". Exemplary instances of these metrics will be discussed at length in the Detailed Description of the Invention section (below). Please note that electronically characterizing is essentially a preferred aspect of electronically storing.

More specifically, "(d) electronically storing a data representation of the responses and of the characterizations, along with a time stamping of at least one of the accepting steps (self-assessment and/or self-characterization), for use in a longitudinal analysis of the client psychological development." relates to memory for use by any of the entities, for transformation into a quantitative or categorical valuation, and/or into an audio and/or visual and/or multi-sensory representation, for evaluation of a current assessment and/or for consideration of real or hypothetical trends, and the like. Again, relevant exemplary instances of these will be discussed at length in the Detailed Description of the Invention section (below). Please note that electronically storing preferably includes electronically calculating at least one score for an assessment selected from the list: the self-assessment response, a combination of self-assessment responses, the self-characterization, any combination thereof, and a combination of all self-assessment responses and all self-characterizations wherein each response and each characterization includes a respective predetermined relative score weighting factor; and that detailed scoring examples and a formula (to calculate each dimension based on each response and it's respective weighting factor) will be given hereinafter.

In addition, the electronically storing preferably firstly includes issuing a respective alert if at least one of the scores is outside of a predetermined range having a respective lower threshold and a respective upper threshold; and secondly preferably includes issuing a respective alert if at least one of the scores is outside of a predetermined range of change from a prior electronic stored assessment value for that score. Likewise, as in these considerations for issuing an alert, the preferred iPAP issues and alarm when any longitudinal analysis reveals an incident valuation outside of respective predetermined upper thresholds, lower thresholds, ranges, and/or acceptable change values.

Furthermore, electronically storing includes electronically communicating with at least one appropriate adviser and the communicating includes (a) providing the at least one adviser with access to the data representation and (b) accepting from the adviser at least one directive selected from the list: (i) amending preferences for accepting goal-relevant self-assessment responses, (ii) amending preferences for accepting self-characterization responses, (iii) directing the client to a computerized interactive psychological intervention protocol (iPIP) or to a micro-intervention function therein, (iv) electronically communicating with the client, (v) electronically communicating with another adviser, and (vi) establishing an electronic communications conferencing with the client and with the another adviser; or the like.

In the context of "electronically communicating with at least one appropriate adviser", a "directive" relates to the adviser either authorizing the protocol to continue according to the respective next micro-assessment steps or to authorize the protocol to transition to at least one different next micro-assessment step; or even to go outside of the adaptive micro-assessment steps to at least one of the options (i) thru (vi), or the like.

Likewise, in the context of "electronically communicating with at least one appropriate adviser", "preferences" relates to a current configuration of requests for client response, which most often means which are the next questions or tasks that the client will be asked to respond to. Thus an adviser may decide that certain areas of the current micro-assessment are important or that certain parts of the recent micro-assessment should be repeated; just as might be the case were the adviser trying to perform the assessment personally. Nevertheless, "preferences" may sometimes mean going outside of iPAP to other programs (such as auto-intervention) or to physical intervention. An example of referral to physical intervention is when the adviser believes that the client is having or headed to a possible suicidal act, or to an act of a criminal nature, or an unacceptable self-destructive act, or the like.

Also, in the context of "electronically communicating with at least one appropriate adviser", "directing" relates to transferring (or opening) an electronic communications linkage with PIP or to a specific section of iPIP; and includes sharing of sufficient client account ID information to allow respective directing back from iPIP to the client's respective then-current iPAP processes, or the like.

Furthermore, in the context of "electronically communicating with at least one appropriate adviser", "electronically" relates to any combination of voice, video, GPS location, requesting and accepting client's electronic sensor readings (such as heart rate, GSR, or the like), etc.

According to one iPAP variation, electronically characterizing (at least one parameter selected from the list: client's response time to any respective question or stimulus or task, client's voice, client's face topology, client's pupil dilation, client's eye tracking, client's GSR/EDA (Galvanic Skin Response or substantially equivalent), client's changes of skin-color, client's respiration, client's heart rate, client's heart rate variability, client's movements, client's brain waves, client's temperature, a combination of any of the aforesaid, and the like) includes monitoring micro-shifts therein. This enables intimate comparisons of stress, truthfulness, and the like—even during a single interactive psychological assessment. An exemplary value of monitoring such micro-shifts is to automatically identify responses that are significantly different than the large plurality of other responses in the same iPAP session. Likewise, noticing that the same response generates this anomaly over a plurality of sessions is noteworthy for the both computer and trainer attention. Here also, relevant exemplary instances of these will be discussed at length in the Detailed Description of the Invention section (below). Please note that, for the preferred iPAP, monitoring micro-shifts includes respectively customizing at least one subsequent request for the goal-relevant self-assessment response in accordance with at least one of the micro-shifts; and/or includes respectively customizing at least one subsequent request for the self-characterization response in accordance with at least one of the micro-shifts.

Now, according to another iPAP variation, accepting responses includes a cluster analysis of variables from the data representation. A cluster analysis is a multivariate statistical portrayal of responses to identify substantially correlated items (which may characterize a client—because these seem to be a single variable in his/her frame of reference), and to describe shifts of clustering (which represent significant changes in the internal-experience worldview perspective of the client). According to one associated iPAP aspect, the cluster analysis is divided into at least two aggregates selected from the list: logical mind, emotional response, physiological response, conscious mind, and subconscious mind—because these aggregates correspond to predetermined assessment models or because a trainer theorizes that these are a reasonable substitute in the context of such a model.

According to another associated iPAP aspect, the cluster analysis is transformed onto a model selected from the list: psychological state model categories, personality model categories, a plurality of goal progress relevant dimension categories, and any combination thereof; because some schools of contemporary psychological assessment modeling view these aspects a substantially independent. In conjunction therewith, according to one enabling iPAP, the accepting the self-assessment responses is modified according to the transformation; which thereby directs the order of iPAP tasks and/or the structure of those tasks.

Likewise in conjunction therewith, according to another enabling iPAP, the accepting the self-characterization responses is modified according to the transformation; which likewise thereby directs the order of iPAP tasks and/or the structure of those tasks. Furthermore In conjunction therewith, according to yet another enabling PAP, the transformation is elected (selected or chosen; albeit including changed or amended) by at least one professional after any of: interviewing the client, reviewing the client's responses, and comparing the aggregates; because the trainer may know (or suspect) that a different iPAP task order or a different iPAP task structure will reveal aspects of the client's psychological profile, which will be more productive for achieving the goal and/or the client's general psychological development. Similarly, the trainer may invoke software modules which facilitate messaging with the client, amending the ongoing iPAP protocol by adding an assessment or a micro-assessment, prescribing or suggesting an intervention, helping the client to progress with an assessment, or the like.

Please note that preferably iPAP's accepting the self-assessment responses is modified according to the transformation, and the transformation is scaled using at least one factor selected from the list: the client's most recent response, the client's previous response, a valuation of the client's attributes and qualities, the clients progress toward the at least one predetermined goal, and any combination thereof. Furthermore, preferably iPAP's accepting the self-characterization responses is modified according to the transformation, and wherein the transformation is scaled interactively in accordance with a personal (human) interactive communication (e.g. text, voice, video).

Furthermore, according to a further iPAP variation, the self-characterization responses include a large plurality of criteria selected from the list: [active:] cheerful, persistent, optimistic, reliable, positive, generous, kind, principled, [connected:] trustworthy, responsible, caring, loyal, appreciative, committed, empathetic, [sustainable:] patient, modest, cooperative, enterprising, visionary, resilient, thrifty, [flourishing:] ambitious, hardworking, self-disciplined, open-minded, purposeful, curious, creative; [other:] kind, loves to learn, critical thinker, leader, practical, implementer, doer, social, attentive to detail, sees big picture, brave, honest, loving, likes to belong to a group, likes to be alone, careful, fair, self controlled, appreciates beauty, purpose oriented, spiritual, introverted, extroverted, fast, thorough, likes simplicity, confident, emotional, intuitive, adaptive, tolerant, listener, playful, likes humor, objective, long-term future oriented, short term oriented, strategic thinker, sees values as important, able to work alone, fast metabolism, eats without gaining weight, logical, focused, calm, precise, consistent, likes to try new things, enthusiastic, lateral thinker, quick decision maker, verbally expressive, enjoys challenges, intuitive, trusts own gut feelings, sees harmony as important, empathetic, artistic, sensitive, auditory, individualistic, expressive, participative, collaborative, organized, grounded, sedentary, adaptive, delegates, shares, translates plan into action, sees past as important, systematic, need all facts before making decision, need time to process information, likes continuity, able to take lots of details, or the like.

Exemplary equivalences to these criteria and to combinations thereof include: love to learn, critical thinker, leader, practical, implementation person, doer, social, pays attention to detail, see the big picture, brave, honest, loving, likes to belong to a group, likes to be alone, careful, fair, self controlled, appreciating beauty, purpose oriented, spiritual, introverted, extroverted, fast, thorough, likes simplicity, confident, emotional, intuitive, adaptive, tolerant, listener, playful, likes humor, objective, long term future oriented, short term oriented, strategic thinker, or the like. Similarly, the client may describe himself (or respectively be describes by a trainer) that: values are important to me; I can work by myself; I have a fast metabolism (I can eat without gaining weight) I am (any of) logical, focused, calm, precise, consistent, someone who likes to try new things, enthusiastic, a lateral thinker, a quick decision maker, verbally expressive, enjoys challenges, intuitive, trust my gut feelings, find harmony important, am empathetic, am artistic, sensitive, auditory, individualistic, expressive, participating, collaborative, communicative, organized, grounded, still, adaptive, delegating, sharing, translate plans into actions, see the past as important for me, systematic, need facts before making a decision, need time to process information, like continuity, have a large capacity for details, or the like.

Also, according to an addition iPAP variation, the self-characterization responses include accepting client assigned importance weighting to a plurality of the self-assessments. Likewise, an iPAP is further including accepting at least one free text response or spoken response from the client; such as a written response or a comprehensible oral response. Similarly, another iPAP is further including accepting at least one free text comment from an appropriate professional; such as a written comment or a comprehensible oral comment.

In addition, a different iPAP is further including at least one interactive software module on an electronic device of the client (such as a personal computer, a smart-phone, a smart-watch, or the like), and the respective module is capable of representing predetermined self-assessment and self-characterization stimulus to the client; at least one interactive software module on a remote electronic system having a robust memory media, and the respective module is capable of electing the respective predetermined stimulus, transmitting a request to respectively present to the client device, and accepting a respective response therefrom; and substantially real time electronic communications between the client's software module and the system. According to one associated iPAP aspect, the at least part of the memory media resides on the client device; which is preferably designated to preserve predetermined aspects of the client's privacy.

Now, according to yet another iPAP variation, the goal relevant motivation includes at least one dimension selected from the list: motivation to use an intervention, motivation to change, and motivation to achieve the goal. Also, according to still a further iPAP variation, the goal relevant belief includes at least one dimension selected from the list: belief that (this process which includes assessments and) an intervention can be effective (or helpful), belief that an intervention can be effective, belief that an intervention can help the user, belief that there can be progress toward the goal, belief that the goal can be achieved by the user, confidence in any of the aforementioned dimensions or in any combination thereof, and a combination knowledge and skills to achieve the goal.

Furthermore, according to still a different iPAP variation, the goal relevant know-how includes at least one dimension selected from the list: knowledge of information regarding any of the steps, people, organization, and intervention that can help to progress toward achieving the goal; knowledge of requirements to implement a change toward achieving the goal; and knowledge and skills to achieve the goal. According to still another iPAP variation, the goal relevant state-of-mind includes at least one dimension selected from the list: general wellbeing, short term state-of-mind during an intervention, level of anxiety, openness to change, openness to be influenced by an intervention, general wellbeing during a period of preparation to change, during a period of trying to achieve the goal, level of depression, mental state, and physical limitations. Now, according to yet a further iPAP variation, the goal relevant activity includes at least one dimension selected from the list: actions repeated in daily life, habits, readiness to act, actions taken to improve readiness to act, readiness to change, actions taken to improve readiness to change, action taken for an intervention, actions taken to progress toward achieving a goal of the at least one goal, actions repeated to form a positive habit, and actions taken to prevent a relapse.

Finally, yet another iPAP is further including the longitudinal analysis of the client psychological development according to at least one quantification of multiple instances of an aspect selected from the list: at least one of the self-assessment responses, at least one of the self-characterization responses, at least one of the metrics, and a correlation of any of the aforesaid. According to one associated iPAP aspect, the longitudinal analysis includes issuing a respective alert if at least one of the quantifications is below a first predetermined threshold or above a second predetermined threshold. According to another associated iPAP aspect, the longitudinal analysis includes issuing a respective alarm if an aggregate of the quantifications is below a first predetermined threshold or above a second predetermined threshold. According to yet another associated iPAP aspect, the longitudinal analysis includes a graphical user interface representation of the quantifications; such as in a variables-to-vectors space representation, or as spatial volume representations of respective assessment valuations, or the like.

DETAILED DESCRIPTION OF EMBODIMENTS iPAP is a computerized assessment system.

iPAP is really about practical empowerment of the client and of the trainer; that is empowerment to change, to improve, to become more enabled, and many similar general goals associated with psychological health and fortitude to engage with ordinary real-world activities and associated experiences.

An empowerment scale is an important aspect of iPAP, which is a highly comprehensive assessment (or scale) to measure such goal oriented determinations as: if a user is ready (empowered) to make specific goal oriented change (such as to start work, reduce weight, stop drinking, help himself to change from a state of depression, to enjoy life, etc). Thus, essentially "readiness for change" in the direction of the respective goal is critical to success for psychological health in general, and for achieving that goal in specific.

It should be appreciated that there are iPAP features that human evaluators can not do, if only because iPAP is a computerized assessment, which can measure the exact response time to answer each question, and therewith analyze if the user is hesitating for this question or task response. Furthermore, iPAP can ask questions in different ways or in opposite ways, to discover if the user is consistent and reliable. Validation of answer consistency was done on paper based evaluations, however iPAP (as a computerized system) can reconfigure the questioning and tasking process to explore (now and later) individual client inconsistencies; by presenting a question to the specific client (user) related to their respective inconsistencies.

For example, as an aspect of exploring the client's "readiness for change", there are at least three query and task accessible (interactive) stage sub dimensions:
1. Pre-contemplation (e.g. the user does not even want to stop drinking, he is not even thinking that maybe it can be good for him to reduce drinking—or cigarette smoking or 0 start working, etc.);

2 Contemplation (e.g. the user is thinking that maybe he should do something about his drinking or smoking or weight, etc);

3. Action (e.g. the user is starting to do some action toward the "goal"—which is now looking for a job or writing CV (curriculum vita—resume) or cutting cigarettes per day or looking for someone who can assist him, etc.).

However, if in the questionnaire, the score for pre-contemplating is high and score for either action is high (or contemplation is high), then this show that there is a contradiction; and the user is not reliable and consistent in his answering.

The iPAP interactive assessment, then creates a question for such case; such as by presenting the user with his two contradictory answers and asking him why he answered the question in this way—even giving him a few possibilities (excuses to chose from and/or or free text), and asking him the question again (with or without any change of the question's phrasing).

iPAP thus gives deeper understanding of the user state of mind in relation to this issues and also provides an analysis about why the user answered in this way (e.g. he is not reliable or was not sure or did not understand, etc.).

It should be noted that a prior art psychological model of readiness for change (potentially used as an assessment instrument) is a linear model having six stages: pre-contemplation, contemplation, preparation, action, maintenance, and termination. However, these six stages are within a single dimension. The present invention adds more dimensions, which then enable analysis of WHY the user is in each stage. These added dimensions include: a dimension relating to the client's level of motivation; another dimension relating to the client's confidence or belief that he can make the change; a further dimension relating to his knowledge regarding how to make the change, etc.

Another iPAP feature substantially combines assessments and interactive treatments; thereby facilitating interactive micro-interventions. For example, in an interactive application for treatment (of Anxiety-Depression—to help an unemployed person to get a job), i PAP improve the user's life through creation of many small assessments, immediately relates to the score on each dimension of the questionnaire, provides the user with a feedback, and/or invokes a "micro-intervention" which is typically followed by another assessment (followed by another relevant micro-intervention, etc.). This can create a very effective interactive treatment—tailored to the specific user personality, emotional state, state of mind, readiness state, preferences, etc.

To increase user motivation, iPAP may engage in giving the user points and/or rewards; such as according to the user's answers, to his progress, and to his actions in real life. Essentially, iPAP can become a fundamental component in a Life Gamification (intervention patent), which accept and responds to data from the user (or OTHERS or sensors) reporting on positive action in the users life and behavior (such as attended a smoking cessation workshop, went to an interview, etc). Thus, and iPAP gamification extension can give the user a reward in the "real-life reflection game", upgrade the user's "game level", assign a user appropriate visual character change badge, etc.

iPAP Empowerment Scale and Indicator

One way to conceptualize iPAP empowerment is by exemplary Dimensions, such as (i) motivation, (ii) belief, (iii) know-how, (iv) state-of-mind, and (v) activity; or the like. These dimensions each have a lower threshold for invoking immediate intervention consideration, and an upper threshold for invoking a respective next appropriate step empowerment intervention. Likewise, the thresholds can be combined, as if the respective scores described a multidimensional volume with a respective lower and upper composite threshold values.

Motivation includes motivation to use the intervention and motivation to change (to achieve the goal). Belief (confidence) includes belief that this intervention is effective (can help him) and belief that he can progress toward (and achieve) the goal. Know-how includes knowledge and information that the user has about the steps or people or organization or information or interventions—that can help him to progress to achieve his goal. By one know-how example, if the goal is to reduce weight, then does the user knows how to join a "weight watcher" support group, or how to find information or people who can help him to reduce weight, etc. By another know-how example, if the goal is to get a job, then does the user know where he can find a list of potential jobs for him, or who can help him to find a job, etc. Turning to knowledge that is required to implement the changes and to achieve the goal, a first example considers if the goal is to reduce weight, then does the user know what and how much he should eat; what and how much activity he can do, etc. By a second requisite knowledge example, if the goal is to get a job, then does the user have qualification and skills for the specific types of jobs that he would like to get; which in turn invokes a skills-set audit, such as valuation of user knowledge of using a computer, communication skills, etc.

State-of-mind and wellbeing include short term state and general state. For example, with regard to short term state-of-mind during an evaluation and a potential subsequent (or substantially simultaneous) intervention, is he too anxious, is he less open minded to change and to be influenced by the intervention, etc. Similarly, regarding general state-of-mind during, this period of preparation to change (to achieve his goal), what is his level of anxiety, his level of depression; what is his metal state—such as after an accident, PTSD, etc.; what is his physical wellbeing, such as that can limit him from achieving his goal (e.g. if there is an injury and his goal is to achieve a medal in sport).

Actions often relate to goal relevant events that repeat in daily life and to personal habits. Thus, regarding readiness to act (to change to get to the goal), at what stage of readiness is the client to make the change, how ready is he now to achieve the goal, etc. For example, maybe he does not even want to stop smoking, or to start working, etc.; or he is aware that it might be better for him, but he is not ready yet; or he would like to first check, what he is to do to progress toward the goal; or he is actively trying to progress or to find out how to achieve the goal; or he has already started to achieve the goal—such as he has stopped smoking for 3 days, or started to work, etc. Another aspect related to evaluation of goal directed action that have already been taken; such as repeating an action—which then is starting to form a positive habit; actions and efforts to prevent relapse—for example, does the user know how to prevent his relapse, etc.

Personality types constitute relevant dimensions for appropriate assessment. Various systems categorize in different ways; and it is not always instantly possible to convolve a transformation from one system to another. For example, since there are Ayerveda oriented assessments, various psychology assessments (e.g. Yung, human dynamics, etc.), often iPAP will enable personality descriptions relevant according to the available intervention services, or according to the intervention services that the client suggests that he is willing cooperate with, etc. It should be noted that the variability provided by iPAP, inclusive of micro reassessments will provide a personality data modeling space which in turn should statistically subdivide a large population of iPAP users in to numerous distinct clusters which would otherwise be categorized into a single model dependent "type". Accordingly, it should be appreciated that cumulative iPAP data will provide a much needed advancement in the art; even if the clinical labeling of respective population clusters proves to be linguistically difficult.

There are five main exemplary iPAP dimensions, which are all important for empowering a person to make important life changes. Life changes can be in any area, such as modifying negative habits (e.g. cease smoking, improving diet), or areas related to career (e.g. returning to work following psychological or physical health problems, etc). Each dimension can be assessed, and an intervention suggested for improvement in the particular dimension. Essentially, iPAP firstly relates to interactive assessment of the user state in all these dimensions; which can be appreciated as an "empowerment scale" (to achieve the goal); and according to a further related embodiment, to interactive computerized intervention, which includes interactive assessment of all the above-mentioned dimension and to intervention (to progress and to improve each of the above-mentioned dimension—according to the specific state of the user in each dimension, etc.).

It should be noted that most of the existing psychological assessment were based on pen and paper; and that typically the computerized version of the assessment just copied the same assessment; to thereby direct the mentor to the same intervention. IPAP really breaks out of this rigid standardization to allow for measuring and properly weighting of individualized nuances that were being lost by prior art assessments—and often missed by mentors relying on those assessments.

Preferably, iPAP is embodied via a computer and mobile telecommunications technology (including a touch screen of a typical mobile device); thereby allowing the client to interact with a micro-reassessment and a respective micro-intervention on an as needed basis. Such real time as-needed iPAP use allows improved measurement of response time consistency, emotion driven hesitation, consistency under stress, or the like. Furthermore, iPAP is preferably enabled to accept data from respective device sensors in the mobile—which adds new possibilities; that were not possible (nether in paper assessment not in face to face assessment). For example, using such sensors, iPAP can check reliability of the user's answers, the confidence of the user regarding the answer, the user's honesty and even the user's emotion regarding the question and the user's answer. For example, an iPAP enabled device can measure the exact time (in microseconds) between presenting the question to the user and his reply. iPAP can thus ask the user immediately after receiving his answer: "Have you hesitated in answering?", and will give him a scale of for user to select his level of hesitation—rather than require him to just a yes-or-no. iPAP "knows" the real time that it took the user and iPAP can compare it to his level of hesitation.

PAP can reconfigure this user's assessment protocol to let him (at some later stage) answer the same question again (or a version thereof) and/or to correct the answers. For example, at the end of a present iPAP assessment session, iPAP can present the user with some or all of his answers, and enable him to "correct" his answers. Nevertheless, iPAP keeps the original answers and compares with these to "understand" why he changed his answer.

Returning to sensor enabled iPAP sessions, iPAP can use the touch screens in mobile tablets to ask the user to respond to a question or task by moving his finger a long a scale with text that can change according to the distance—rather than using a standard paper assessment emulating heading of "from 1 to 5" etc.). Moving to other formats which perhaps superseded paper and pencil assessment testing formats, iPAP can present photos instead of or in addition to text; such as to ask the user to choose the photo that represent his mood now. iPAP can ask him to answer by voice and iPAP can then analyze the users voice using voice recognition techniques to assess his emotion, confidence, reliability, etc., even to the resolution of each specific question. iPAP can present video clips—both as part of the question, part of the intervention, and as education material. iPAP can use face recognition to analyze emotion during the questions, answers, and intervention. iPAP can create interactive "paths" for each user—according to his reply; and according to his assessment in each stage. Thus, iPAP can continue in a respectively user-responsive way to present the next intervention and assessment; so each user will receive a specific path of several small assessment interventions that are relevant exactly to him. iPAP can let the user chose specific preferences and intermediate goals; regarding both the intervention and the goal that he would like to achieve.

iPAP can also integrate the user goals with the organization goals; for example, if the intervention is funded by a government to help the user to overcome PTSD and to get a job—albeit the user would like to overcome the PTSD but may simultaneously prefer to get compensation and not to start working. Accordingly, iPAP can merge the user and organizational objectives to help the user to overcome his PTSD and to motivate him to get a job.

According to still another iPAP aspect, because of mobile technology—both the assessment and the intervention can be used on mobile phone during specific day-to-day user situations. Thus, unlike intervention with psychologist, the user can use some specific interventions (which are tailored to his events) in his specific daily situation; for example, in a restaurant—before choosing what to eat from the menu; in his school—before the exam; before an interview for a job; etc.

General Algorithm to categorize the multidimensional scoring and presenting to the user
and/or his mentor (trainer/therapist):
For "change" which is to respectively reach the at least one predetermined goal:
IF dimension A (motivation to change) has categories (e.g. a=4: negative 0, neutral 1,
positive 2, very positive 3); And IF dimension B (confidence or belief that they can change) has b categories (e.g. b=3: no confidence 0, some confidence 1, very confidence 2); And IF dimension C (Action state—ongoing activities to accomplish the change) has categories (e.g. c=3: no action yet 0, some initial action 1, proper action 2); And IF dimension D (state of mind—which can contribute to or distort progress to reaching the goal(s)) has d categories (e.g. d=8: very severe depression and anxiety 0, moderate depression and anxiety 1, mild depress and moderate anxiety 3, no depression moderate anxiety 4, mild anxiety 5, no anxiety and depression 6, very happy 7); And IF dimension E (relevant knowledge/skills—understands what is and what will be needed to change) has e categories.
THEN iPAP enables a virtual table or tables such that:
The numbers of entries (rows) in the table: a×b×c
IF the specific category of user 1 to dimension A is A1 (e.g. 2 positive) and IF the specific category of user 1 to dimension B is B1 (e.g. 1 some confidence) and IF the specific category of user 1 to dimension C is C1 (e.g. 0 not yet action)

THEN this user entry number (row) in the table is; 1+A1+B1×b+C1×b×c

Alternately: if we prefer an exemplary 5 dimension table, then the number of entries are a×b×c×d×e and the specific user row entry in the table is 1+A1+B1×b+C1×b×c+D1×b×c×d+E1×b×c×d×e As an exemplary feedback iPAP strategy is:
a) to be honest-not to present anything which is not true;
b) to present to the user his positive answers (in other words) in order to increased his confidence and motivation
c) if he answered a negative answer, to present him with multiple choices of positive statements which are related to his negative answer and to let him choose all the relevant one.

Later iPAP can present to him the positive answers that he has selected as a positive list with 'well done" as a symbolic text "reward", etc iPAP's purpose is to help and to empower the user to progress in the levels and categories of all the relevant dimensions; in order to achieve the agreed goal or to progress toward it (e.g. reduce some weight; to start specific actions to prepare himself for the goal, etc).

iPAP can both use expert knowledge and experience to choose the priorities for which areas and dimensions are more important to progress at this stage of the user; and also ask the user his preferences and priorities.

Similarly: Existing readiness to change is more a linear model in which the user is assessed; in order to discover in which category he is regarding his readiness to change toward the goal (e.g. doing exercises, stop smoking, reducing alcohol, start working, etc.). The general consensus define 5 or 6 ready-to-change stages: pre-contemplation, contemplation, preparation, action, maintenance, and termination; although some theories ignores termination and/or preparation). Exemplary iPAP suggests that it is not a linear model but a multidimensional model that in order to progress toward the goal and achieve it we have to progress in each of the dimensions.

Algorithm for scoring and feedback for a multidimensional questionnaire: It should be noted that for a preferred iPAP, the primary purpose of the assessment is to assess the states of the users with regard to the specific "goal" which the user (or people who want to help him) would like to achieve or to progress toward (such as: reducing weight, healthier eating, getting a job for unemployed, reducing anxiety level, becoming more happy, improve wellbeing, etc.); in order to select and customize for him the most effective solution, an intervention to progress toward achieving the goal, and to "measure" the progress.

Step a: each question can have 5 answers 1-5: the score is the number

Step b: each question can contribute to a dimension—so we multiply the question score with the weight of contribution to each dimension. In our case it is either 0 or 1 for for PC, C, A—And add together the total of each dimension.

Step C: convert negative dimension to positive; PC to Will to work: W=24 minus PC Step D: optional: each dimension score can be divided to general categories, In our case: negative, positive and very positive. (e.g. less than 13 is negative as the user on average has more negative than positive answers. More than 18 per category is very positive.)

Step E: Algorithm for scoring and feedback to a multi dimensional questionnaire 1. If the questionnaire has 3 dimensions for example;

Dimension 1: will to work (in general questionnaires—motivation level) W

Dimension 2; Contemplation or Confidence level, or considering level (in general questionnaires confidence level C)

Dimension 3: Action level—A (we can add later dimension 4—knowledge/skills

And dimension 5—state of mind—anxiety/depression/stress level)

Although the level of each one is a continuum we can divide it to specific levels and also general categories such as: negative, positive, very positive.

If in our example we are dealing with 3 dimension and each one 3 general categories, and we are looking at 3 dimension space therefore we can divide the space into 3×3×3 sub spaces or category. Using the exemplary algorithm decision table (FIG. 4), according to the 3 categories in each dimension we can find the exact final category for the user. Each row represent specific final category for which we can give specific name, feedback and intervention, which can take into account the 3 sub dimensions levels.

Comment 1: we can create dimensions which are almost orthogonal to each other—e.g. minimum correlation between these dimensions (such as level of knowledge and level of anxiety); or by purpose create dimensions which have correlation or anti correlation—to check the reliability and consistency of the users answers.

For example: dimension 1: does not want to work and the dimension 2 Willing to work. Comment 1: For readiness to work the above table represents 3 dimensions.

Turning now to FIG. 5, in order to simplify the process and tables if there are more than x dimensions (e.g. x=3 in our case) instead of creating a 5 dimensional table, we can work first with 3 dimensions (as in table 5) and select the users who are in a specific category (e.g. action category) and continue with screening for the next dimension/s. For example knowledge or skills we will create in the same way another a 2 dimensional table for levels of skills and actions. Programming Algorithm:

In each dimension: level 1 (e.g. negative <13) is 0; level 2 (eg positive 13-17) is 1 and 790 level 3 (eg very positive 18-20) is 3.

So the number of the row is calculated as: 1+W+Cx3+ Ax9; example: If Will is 18 (category 2) and Contemplate is 14 category 1) and Action is 15 (category 1) than the row number is 1+1x3+1x9=13

Figure 2:
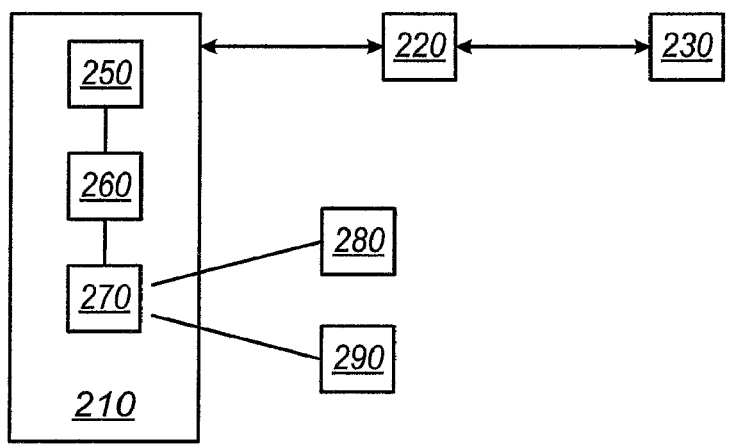
FIG. 2 illustrates a schematic view of a computerized interactive psychological assessment protocol module.

Returning now to FIG. 2, the present invention also relates to embodiments of a computerized interactive psychological assessment protocol (that is iPAP—Mutatis Mutandis) module, preferably for use in conjunction with a computerized interactive psychological intervention protocol module, and the assessment protocol module includes: software (210) accessible to a mobile electronic communications enabled device (220) that has a predetermined interactive media (230) interfacing with a client. This software is capable of (firstly) performing (240) at least one step selected from the list: (a) for at least one predetermined goal, accepting (250) goal-relevant self-assessment responses from the client, substantially regarding at least three of the client's respective dimensions which are selected from the list (i) motivation, (ii) belief, (iii) know-how, (iv) capability, (v) state-of-mind, (vi) activity, and (vii) expectation to achieve the at least one predetermined goal by a prespecified time; and (b) accepting (260) self-characterization responses from the client, substantially regarding the client's respective personality attributes, qualities, and preferences. Furthermore, this software is capable of (secondly) performing (270) at least one step selected from the list: (a) electronically storing (280) a data representation of the respective responses and characterizations, along with a time stamping of at least one of the acceptings, for use in a longitudinal analysis of the client psychological development; and (b) electronically communicating (290) a data representation of the respective responses and characterizations, along with a time stamping of at least one of the acceptings, for use in a longitudinal analysis of the client psychological development.

While it should be appreciated that interactivity is preferably "Real Time" communications, there are many gradation of importance in psychological assessment (and in psychological intervention). Thus, on the one hand, real time may be according to the best capabilities of electronic communications and computer bandwidth; on the other hand, real time may be at the discretion of the respective client's iPAP (or iPIP) adviser. Accordingly, for the preferred embodiments, electronically communicating a data representation includes interactively sharing the representation with at least one adviser.

According to one variation embodiment, interactively sharing the representation with at least one adviser includes establishing interactive communications between the client and an adviser of the at least one advisers. Furthermore, it is preferable that establishing interactive communications between the client and an adviser of the at least one advisers includes at least one information mode having representation on the device that is selected from the list: voice, text, audio, visual, adviser directed linkage to an adviser selected segment directed to accepting a specific goal-relevant self-assessment response or a specific self-characterization response, and adviser directed linkage to an adviser selected segment of a computerized interactive psychological intervention protocol module. Now, according to another variation embodiment, interactively sharing the representation with at least one adviser is automatically activated when the client presents a response that is equivalent to a predetermined alert or alarm condition. Furthermore, it is preferable that the response is a predetermined combination of responses.

According a further embodiment of the module, interfacing with a client further includes interactively defining at least one new goal. According another further embodiment of the module, the software is further capable of storing questions or tasks for client response, selecting a next question or task for client response, and presenting the selected next question or task to the client. According yet another embodiment of the module, the software is further capable of partially evaluating a plurality of client responses including at least one recent response.

Figure 3:
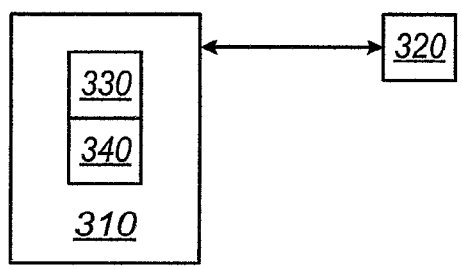
FIG. 3 illustrates a schematic view of a computerized interactive psychological assessment protocol module development method.

Turning to FIG. 3, the present invention also relates to embodiments of a computerized interactive psychological assessment protocol module development method (310), preferably for use in conjunction with a computerized interactive psychological intervention protocol module development method (320), and the assessment protocol module development method includes: (a) selecting (330) an object and (b) recursively nesting (340) the object into a meta-object. Preferably, the selective and respective nesting is to the extent/depth that the recursion is appropriate for the object and data—however this method allows exploration into next iteration simulation hypothetical—at least according to the extent that the client is known and/or is object-similar to other individual or aggregated client-case instantiations.

Essentially, this development method empowers the practitioners of iPAP, iPIP, and of other protocols (appreciated by the ordinary person practicing the psychological assessment and/or intervention arts) to express and actualize these protocols in a manner akin to Object-Oriented Programming (OOP); which is a programming paradigm that is "organized around objects rather than actions, and around data rather than logic"—something much more facile for the applications described herein than respective considerations of assessment and/or of intervention as a bundle of non-OOP input-process-output threads.

A most notable aspect of this transformation to objectification, according to the present invention, is that existing limits (to both complexity and scalability of computerized interactive psychological protocols) are overcome; which in turn allows expansion of these computerized products to new applications for clients who are more typical of real life diversity cases than of rigidly categorized classical textbook-type clinical cases. More particularly, since aspects of the present invention are actively directed to increasing dimensionality (unlike prior art simplification/categorization directed models—that is limitation or reduction of dimensionality), our OOP type module development method allows practitioners to advance the iPAP and iPIP type arts.

Simply stated, the recent prior art literature seems to abound in examples of using OOP languages to program specific psychological application—but surprisingly does not seem to present any example of using the OOP paradigm to transform psychological terms and data into an OPP language, per se; even though such a language would be much easier for practitioners to navigate and to dynamically enhance than virtually all of the OPP programming language implemented psychological assessment and/or psychological intervention application packages.

Now, turning to the (iPAP and/or iPIP) Object Oriented Structure, as applied in the method.

1. The small entity we call "object".

Object can be text, photo, audio, video, assessment, exercises, to do list, etc.

As in OOP, per se, we can add other types of objects which are initialized by the user such as: ask help from the mentor by text, voice, etc. and objects which are replies or push or text from the mentor.

2. We define micro assessment as any interaction which we have to ask the user something back to us, that we can analyze, and assess something about the user or his stat The assessment can be one question or any combination of questions. The questions can be any combination of text, voice-over, any type of choice such as radio, multiple choice, free text, selecting photo, etc 3. Based on some algorithm operable upon the OOP-type domain, which will assess the assessment results, there will be a score/s; and based on this score/s the program will decide what object to present next to the user.

4. The user can receive tasks/to do lists some of which are locked until he finished the previous one.

5. Few objects together can be defined as one module, and one or more modules can be a session.

6. An app can be one or more sessions. If the app is more than one session this is likewise defined as a protocol.

7. We apply an OOP-type characterization to define how we can manage users access including password, that can be managed in a database external to the app, so that this password can be released to the user in a process that we define later, for example, it can be free to the user, but an authorized person (mentor) can release the password or the password can be bought, or can be revealed when the user gets to a specific level.

Finally, while the invention has been described with respect to specific examples, including presently preferred modes of carrying out the invention, those skilled in the art will appreciate that there are numerous variations and permutations of the above described protocols, methods, systems and techniques that fall within the spirit and scope of the invention as set forth in the appended claims.

The invention claimed is:

1. A computerized interactive psychological assessment system, said system including:
   a computerized system including a memory storing one or more predetermined interactive media representing a series of self-characterization questions to be answered by a user,
   wherein said series of self-characterization questions involve at least one predetermined goal,
   wherein said series of self-characterization questions includes at least one sub-series of multiple questions directed toward each of at least two psychological dimensions, said sub-series including at least one of:
   a first sub-series of questions directed toward a will or motivation dimension to address said goal dimension;
   a second sub-series of questions directed toward a confidence or belief dimension to achieve said goal dimension;
   a third sub-series of questions directed toward an action or activity dimension toward said goal dimension;
   a fourth sub-series of questions directed toward said will or motivation dimension to implement the recommended interventions to address said goal dimension;
   a fifth sub-series of questions directed toward a confidence or belief dimension that the specific intervention will help them to achieve said goal dimension;
   a sixth sub-series of questions directed toward said action or activity dimension that are recommend to implement toward said goal dimension;
   a sixth sub-series of questions directed toward a level of know-how dimension which the user has toward said goal dimension;
   a seventh sub-series of questions directed toward a state of mind dimension of the user toward said goal dimension;
   an eighth sub-series of questions directed toward level of anxiety dimension of the user; and
   a ninth sub-series of questions directed toward level of depression dimension of the user;
   a computer-controlled user interface, wherein said user interface displays to said user said predetermined interactive media representing a series of self-characterization questions to be answered by said user,
   wherein said user interface includes an input accepting and recording responses to said series of questions from said user,
   wherein said computerized system includes a video camera directed toward the face of said user to obtain a video image of said user,
   wherein said computerized system determines from said video image of said user and records in said memory, as a question-specific user physiological response, the physiological response of the user observed at least between when each of said series of questions is displayed on said user interface and when an input is received on said user interface in response to the displayed question,
   wherein said computerized system identifies and records in said memory one or more questions having a question-specific user physiological response that is significantly different from a large plurality of other question-specific user physiological responses,
   wherein said computerized system determines a score for said at least one sub-series of questions, said score representing the score of the level of the dimension associated with said sub-series as reported by said user,
   wherein said computerized system uses said score for said at least one sub-series of questions and said user respective response physiology response to determine a psychological assessment of said user with regard to said predetermined goal.

2. The system of claim 1, wherein said computerized system determines and records in said memory, as a question-specific user physiological response data, at least one of the pulse rate, the heart rate, and changes in the pulse rate or heart rate of said user during the time when said at least one series of questions is displayed on said user interface and the time when an input is received on said user interface in response to the displayed question.

3. The system of claim 1, wherein said computerized system determines and records in said memory, as a question-specific user physiological response data, changes in the image of the pupil of the eye of said user during the time when said at least one series of questions is displayed on said user interface and the time when an input is received on said user interface in response to the displayed question.

4. The system of claim 1, wherein said computerized system determines and records in said memory, as a question-specific user physiological response data by performing facial analysis of said user using said video camera during the time when said at least one series of questions is displayed on said user interface and the time when an input is received on said user interface in response to the displayed question.

5. The system of claim 1, wherein when said score is high in two or more of said dimensions, said computerized system causes said computer-controlled interface to again display the sub-series of questions associated with said two or more of said dimensions, and then records in memory said user response to said questions.

6. The system of claim 1 wherein, when determining said score for said at least one sub-series of questions, said computerized system additionally uses a change in the pulse of said user.

7. The system of claim 1 wherein, when determining said score for said at least one sub-series of questions, said computerized system additionally uses a change in at least one of the pulse rate and the heart rate of said user.

8. The system of claim 1 wherein, when determining said score for said at least one sub-series of questions, said computerized system additionally uses a change in breathing respiration of said user.

9. The system of claim 1 wherein, when determining said score for said at least one sub-series of questions, said computerized system additionally uses a change in eye pupil size of said user.

10. The system of claim 1 wherein, when determining said score for said at least one sub-series of questions, said computerized system additionally uses a change in at face topology of said user.

11. The system of claim 1 wherein, when determining said score for said at least one sub-series of questions, said computerized system additionally uses a change expression of said user.

12. The system of claim 1 wherein, when determining said score for said at least one sub-series of questions, said computerized system additionally uses a change in the skin color of said user.

13. The system of claim 1 wherein said responses to said series of questions recorded by said user interface input represent verbal responses.

14. The system of claim 13 wherein, when determining said score for said at least one sub-series of questions, said computerized system additionally uses changes in the verbal intonation of said user.

15. The system of claim 1 wherein said user respective physiological response is a change in said user's heart rate.

16. The system of claim 1 wherein said user respective physiological response is a change in said user's heart rate variability.

17. The system of claim 1 wherein said user respective physiological response is a change in said user's skin color.

18. The system of claim 1 wherein said user respective physiological response is a change in a combination of two or more of said user's heart rate, heart rate variability, and changes in said user's skin color.

19. The system of claim 1, wherein said computerized system determines from said video image of said user and records in said memory, as a question-specific user physiological response, the physiological response of the user observed when each of said series of questions is displayed on said user interface.

20. The system of claim 1, wherein said computerized system determines from said video image of said user and records in said memory, as a question-specific user physiological response, the physiological response of the user observed when an input is received on said user interface in response to the displayed question.

* * * * *